United States Patent [19]

Tabor

[11] 4,325,366
[45] Apr. 20, 1982

[54] VALVE AND METHOD FOR USE WITH A TRACHEOTOMY TUBE

[76] Inventor: Carl J. Tabor, 9845 Reavis Rd., St. Louis, Mo. 63123

[21] Appl. No.: 166,345

[22] Filed: Jul. 7, 1980

[51] Int. Cl.³ ............................................ A61M 25/00
[52] U.S. Cl. ................................ 128/207.16; 137/517
[58] Field of Search ...................... 128/207.16, 207.12, 128/206.15, 205.24, 152, 348, 274; 137/517; 3/1.3

[56] References Cited

U.S. PATENT DOCUMENTS

| | | | |
|---|---|---|---|
| 2,804,076 | 8/1957 | Giraudon | 128/207.16 |
| 2,948,296 | 8/1960 | Thorburn | 137/517 |
| 3,137,299 | 6/1964 | Tabor | 128/207.16 |
| 3,683,931 | 8/1972 | Che Lucci et al. | 128/207.16 |
| 4,040,428 | 8/1977 | Clifford | 128/207.16 |

*Primary Examiner*—Henry J. Recla
*Attorney, Agent, or Firm*—John D. Pope, III

[57] ABSTRACT

A valve and method for use with a tracheotomy tube is presented wherein a flexible diaphragm is located a predetermined distance from a valve seat, the diaphragm being sized to allow air to flow around its periphery in either direction responsive to normal breathing through a tracheotomy tube, and to evert into sealing engagement with the valve seat to block air flow out of the tracheotomy tube responsive to air flow above that present in normal breathing. The diaphragm is in one end of a first barrel and the valve seat is in a second barrel sized to be inserted into the first barrel around the periphery of the diaphragm. Threads are provided between the barrels for adjusting the distance between the diaphragm and the valve seat by rotation of the second barrel within the first barrel. The valve may be inserted into a flexible base having a flexible flange for attachment to the paratracheal skin around the stoma of the patient. A shower shield and filter are also presented for use with the valve and base.

16 Claims, 4 Drawing Figures

VALVE AND METHOD FOR USE WITH A TRACHEOTOMY TUBE

The present invention relates to appliances for use with a tracheotomy tube, and more particularly to a valve and method for use with a tracheotomy tube.

Many times where there is an obstruction in the nose, mouth or upper portion of the windpipe, it is necessary to add a by-pass air passageway through the neck of a patient to the windpipe in order that the patient may breathe. Diseases, such as cancer of the larynx, can require a tracheotomy for allowing the patient to breathe through an opening in his throat as part of the treatment of the disease.

My U.S. Pat. No. 3,137,299 issued June 16, 1964 provide a tracheotomy tube which is inserted into the stoma or opening through the neck to the windpipe of the patient and which has a one-way valve allowing the patient to breathe in through the tracheotomy tube and which closes allowing the patient to breathe out through his nose and mouth and to perform other functions as coughing and speaking.

Many times the breathing of the patient is so impaired that he must both inhale and exhale through the tracheotomy tube. In these cases it is still desirable to include a valve which may be closed allowing the patient to cough or to inject air into the esophagus or hypopharynx to allow speech. In the past this has been done by providing a button in the stoma which allows the patient to both breathe in and out through the tracheotomy tube and to occlude or close off the stoma with his hand. This is undesirable where the patent may need both hands such as in his occupation. This is also undesirable because occluding the stoma with his hand can result in contamination of the stoma or the air which the patient breathes.

Other devices have been made to perform this function automatically but they typically consist of complicated valve mechanisms which hang from the stoma on tubes or are otherwise bulky, calling attention to themselves to the embarrassment of the patient.

It is an object of the present invention to provide a simple, lightweight and small valve usable with a tracheotomy tube which allows the patient to breathe in and out of the stoma in a normal fashion but which closes during expiratory pressure increases allowing the patient to cough or to inject air into the esophagus or hypopharynx for speech. It is another object of the invention to provide a valve having a valve seat and a flexible diaphragm between the valve seat and the stoma which allows air to pass through an opening in the valve seat around the periphery of the flexible diaphragm during normal breathing, but which everts upon an increased pressure in the tracheotomy tube above that present in normal breathing to sealingly engage with the valve seat thereby blocking passage of air from the tracheotomy tube. It is a further object of the invention to provide means for adjusting the distance between the valve seat and the flexible diaphragm thereby increasing the rate of flow of air through the valve before it is closed such as would be present during heavy exertion by the patient. It is a further object of the invention to provide a base which may be easily attached to the paratracheal skin around the stoma eliminating in indwelling cannula extending into the stoma. It is a further object of the invention to provide a shield usable with the valve and base for preventing entry of water when the valve is worn in a shower and to provide a filter usable with the valve and base for filtering the air breathed by the patient when the patient is in a polluted or contaminated atmosphere. Other objects and features will be in part apparent and in part pointed out hereinafter.

The invention accordingly comprises the constructions and methods hereinafter described, the scope of the invention being indicated in the following claims.

In the accompanying drawings, in which one of various possible embodiments of the invention is illustrated, FIG. 1 is a cross-sectional view showing the base and valve of the invention;

Corresponding reference characters indicate corresponding parts throughout the several views of the drawings.

Figure 1:
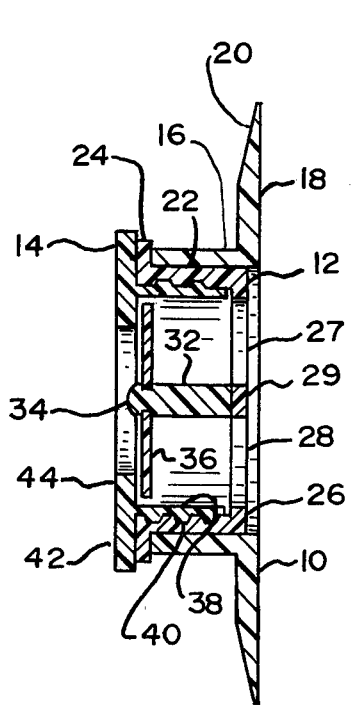

FIG. 1 is a cross-sectional view showing a base 10, a valve body 12 and a valve insert 14. The valve body 10 has a tubular portion 16 and an outwardly directed flange 18. Base 10 is made of a pliable plastic material such as silicone in order that tubular portion 16 may easily receive valve body 12 inserted into it and flanged portion 18 may easily conform to the paratracheal skin of the patient. A portion 20 of flange 18 can be tapered to facilitate flange 18 conforming to the skin of the patient.

Valve body 12 has a barrel 22 which is inserted into the tubular portion 16 of base 10. Connected to the free end of barrel 22 which extends beyond tubular portion 16 is an outwardly directed flange 24. Flange 24 acts as a stop to stop the insertion of barrel 22 into base 10.

Figure 2:
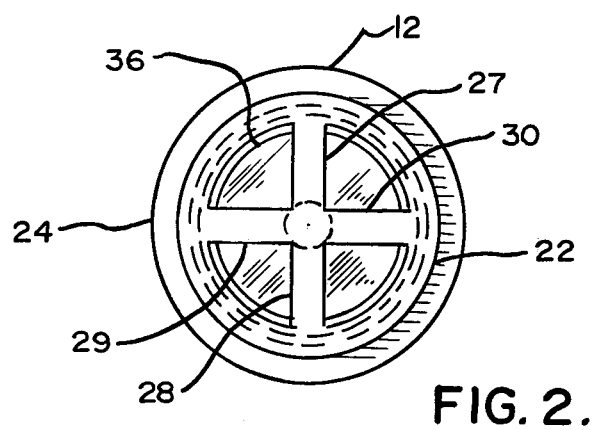
FIG. 2 is an elevational view of the body of the valve when viewed from the end closest to the patient.

A narrow inwardly turned flange 26 is provided at the end of barrel 22 which is inserted into base 10. A plurality of arms 27, 28, 29 and 30 all have one end attached to flange 26 and are connected to each other in the center of barrel 22 to form a spider as shown in FIG. 2. A center post 32 is connected at one end to the center of the spider formed by arms 27–30 and extends on the central longitudinal axis of barrel 22 to the free end of barrel 22. It will be understood that this configuration centers post 32 in the passageway through barrel 22 while still allowing air to flow freely past the spider formed by arms 27–30 permitting a free flow of air through barrel 22.

A button 34 is located on the free end of center post 32 over which is positioned a flexible valve diaphragm 36. As will be seen, diaphragm 36 is undersized a sufficient amount to allow free passage of air around its periphery in either direction, but which everts when a sufficient quantity of air is exhaled by the patient against the backside or patient side of diaphragm 36. Diaphragm 36 is made of a flexible plastic and may include a nylon net embedded in the plastic to give sufficient rigidity to diaphragm 36 so that it will not evert during normal breathing, but which is flexible enough to allow diaphragm 36 to evert responsive to a desired overpressure.

Valve insert 14 has a barrel 38 which is inserted into the free end of barrel 22. Threads 40 are located between barrel 38 and barrel 22 so that barrel 38 may be screwed into barrel 22 a variable amount as desired.

At the free end of barrel 38 which extends from barrel 22 is an outwardly directed flange 42 and an inwardly directed annular shoulder 44. The inside surface 46 of annular shoulder 44 acts as a valve seat for flexible diaphragm 36 as is shown in FIG. 3.

The diameter of the opening through annular shoulder 44 is smaller than the diameter of diaphragm 36. It will thus be understood that when diaphragm 36 everts, its periphery forms a sealing engagement with valve seat 46 on the inner surface of shoulder 44 and that additional pressure being exhaled by the patient increases the sealing engagement between the periphery of diaphragm 36 and valve seat 46. When the pressure of the air exhaled by the patient is reduced sufficiently as at the end of a cough or when the patient finishes speaking, diaphragm 36 returns to its original position as illustrated in FIG. 1. Both in and out breathing of the patient can then be resumed through the central opening in annular shoulder 44, around the periphery of diaphragm 36 and past the spider formed by arms 27–30.

FIG. 2 is an elevational view of valve body 12 as viewed from the inside or patient side of the valve body looking outwardly. The spider formed by arms 27–30 is shown which supports diaphragm 36 in the center of barrel 22.

Figure 3:
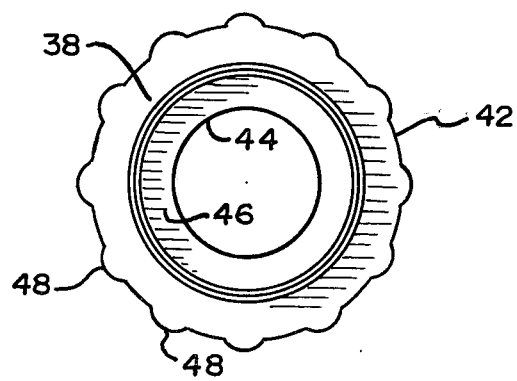
FIG. 3 is an elevational view of the valve insert when viewed from the end closest to the patient.

FIG. 3 is an elevational view of valve insert 14 as would be seen looking from the patient's side of the valve outwardly. Outwardly directed flange 42 has probuterances 48 regularly spaced around its periphery which extend slightly past the sides of flange 24 of valve body 12. These protuberances facilitate the manual rotation of barrel 38 within barrel 22. Both valve body 12 and valve insert 14 can be made of hard lightweight plastic which may be easily cleaned or inexpensively and easily replaced by the patient.

The rate of air which passes around the periphery of diaphragm 36 when air is exhaled by the patient before diaphragm 36 everts may be adjusted by screwing barrel 38 inwardly or outwardly by rotation. This simple adjustment allows the patient to exert himself, such as walking upstairs or engaging in some other physical activity, without prematurely closing the valve and occluding the stoma. When the patient returns to his normal activity, he may simple screw barrel 38 into barrel 22 to return the valve to a more sensitive setting.

The valve setting also sets the closing of the valve at the same point. This eliminates careless occlusion by the patient which allows air to escape and decreases speech intelligibility, or heavy-handed occlusion which may distort the tracheo-esophageal communication and choke off the voice.

Figure 4:
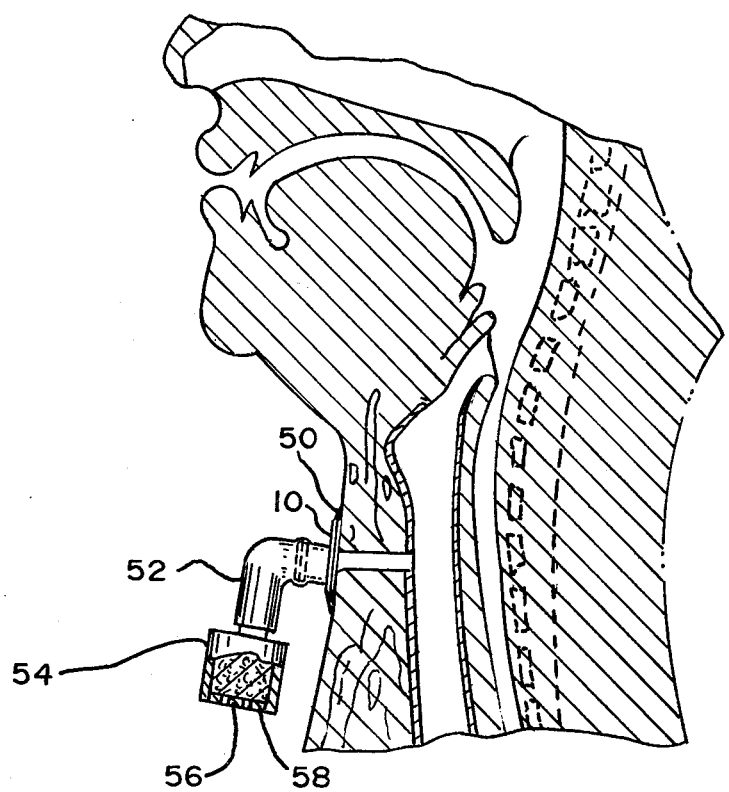
FIG. 4 is a diagrammatic sketch showing the valve and base forming a tracheotomy tube with a shower shield and filter both attached being worn by a patient.

Valve 12, 14 can be sized to be inserted or used with a known tracheotomy tube such as that shown in my U.S. Pat. No. 3,137,299 as well as with base 10 shown in FIG. 1. Use of the valve with base 10 eliminates an indwelling cannula and the potential problems of tracheitis, dilation and air escape. FIG. 4 shows base 10 applied to the paratracheal skin around the stoma of a patient by double-sided surgical tape 50 between the skin of the patient and flange 18 of base 10.

Also shown in FIG. 4, a tube 52 having a bend is sized to slip over protuberances 48 of valve insert 14 and base 10. This tube is then turned so that its outlet is pointed downwardly to allow a patient to take a shower without danger of water entering his lungs through the stoma.

A filter cannister 54 also shown in FIG. 4 partially broken away, has a perforated bottom 56 and filter medium 58 within. The filter medium 58 may be of any known construction or may be a cartridge type filter. Filter cannister 54 which is easily inserted into tube 52 provides a filter for use by the patient when in a polluted or toxic atmosphere. If preferred it can be slipped over protuberances 48 rather than inserted into tube 52 where tube 52 is not employed.

Valve body 12 may be easily removed from tubular portion 16 of base 10 for cleaning. In an emergency where the valve becomes blocked, the patient can easily and quickly remove the valve to restore normal breathing even in a panic condition caused by blocked breathing. Base 10, valve body 12 and valve insert 14 may all be made of plastic material which is extremely lightweight and which may be easily cleaned. If the base or the components of the valve become damaged or unusable they may be easily disposed of and inexpensively replaced by the patient.

It will thus be understood that the tracheotomy tube and valve disclosed allows a patient to engage in normal occupations and activities with a minimum of inconvenience. The valve allows normal breathing through the stoma in the patient's neck while allowing the patient to cough or to speak by merely exhaling at a higher rate than normal.

In view of the above, it will be seen that the several objects of the invention are achieved and other advantageous results obtained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A valve for use with a tracheotomy tube comprising a valve body having an air passageway therethrough, said valve body including means for connecting said passageway with a tracheotomy tube, a post in said air passageway, means for centering said post in said air passageway and allowing passage of air through said air passageway, flexible diaphragm means whose center is attached to said post and sized to fit within said air passageway, and a valve seat at one end of said air passageway and spaced a predetermined distance from said diaphragm means, said valve seat having an opening therethrough smaller than said (membrane) diaphragm means, said flexible diaphragm means (operable for allowing) being so constructed that it allows air to flow around its periphery through said air passageway in either direction when the air velocity is at a rate present while breathing normally through said tracheotomy tube and (operable for everting) everts into sealing engagement with said valve seat when air is exhaled through said tracheotomy tube at a rate above that present when breathing normally thereby blocking said air passageway.

2. A valve according to claim 1 wherein said valve seat is an annular shoulder.

3. A valve according to claim 1 further comprising means for adjusting the distance between said valve seat and said flexible diaphragm means for adjusting the rate of air flow around said flexible diaphragm means before said air passageway is blocked.

4. A valve according to claim 3 wherein said valve body has a first barrel and said flexible diaphragm means is centered at one end thereof, said valve seat has a second barrel with an annular shoulder in one end, the other end of said second barrel sized to be inserted into said first barrel around the periphery of said flexible diaphragm means, and said adjusting means comprises helical threads between said first and second barrels for allowing said second barrel to be screwed a variable distance into said first barrel for varying the distance between said annular shoulder and said flexible diaphragm means.

5. A valve according to claim 4 wherein said centering means is a plurality of arms forming a spider at the end of said first barrel opposite said flexible diaphragm means, and said center post is connected at one end to the center of said spider and extends to said flexible diaphragm means on the central longitudinal axis of said first barrel.

6. A valve according to claim 5 wherein said second barrel has an outwardly directed flange on its free end, said outwardly directed flange having protuberances regularly spaced around its periphery and extending outwardly past the sides of said first barrel for facilitating manual rotation of said second barrel within said first barrel.

7. A valve according to claim 6 further comprising a tube sized to sealingly fit over said protuberances and said first barrel, said tube having a bend for shielding the air passageway through said valve body thereby blocking the entry of water when said valve is worn in a shower.

8. A valve according to claim 7 further comprising a filter connected to said tube for filtering air entering the air passageway through said valve body.

9. A method of blocking air flow through a tracheotomy tube responsive to a predetermined elevated pressure in said tracheotomy tube comprising centering a flexible diaphragm in a flow passageway connected to said tracheotomy tube that is constructed to allow air to flow around its periphery through said flow passageway in either direction when the air velocity is at a rate present while breathing normally through said tracheotomy tube and everts into sealing engagement with said valve seat when air is exhaled through said tracheotomy tube at a rate above that present when breathing normally thereby blocking said air passageway, adjustably locating a valve seat a predetermined distance from said flexible diaphragm, allowing air flow through an opening in said valve seat and around the periphery of said flexible diaphragm in either direction when the rate of flow of air through the tracheotomy tube is that present while breathing normally, and everting said flexible diaphragm into sealing engagement with said valve seat for blocking the flow of air out of said tracheotomy tube responsive to pressure in said tracheotomy tube greater than that present while breathing normally.

10. A tracheotomy tube comprising a base having a tubular portion and an outwardly directed flanged portion, said flanged portion made of flexible material for sealing engagement with the paratracheal skin around the stoma of a patient, a valve body inserted into the tubular portion of said base, said valve body comprising a first barrel having a first end sized for insertion into the tubular portion of said base, a plurality of arms in said first barrel forming a spider in said barrel, a post attached at one end to the center of said spider and extending along the central longitudinal axis of said first barrel to the second end of said first barrel, flexible diaphragm means attached to said post and centered in said first barrel at right angles to said post, a second barrel having a first end slidably inserted into said first barrel, said second barrel having an inner diameter slightly larger than the diameter of said diaphragm means thereby defining an annular space around the periphery of said flexible diaphragm means, helical threads between said first and second barrels wherein said second barrel is operable to be screwed a variable distance into said first barrel, said second barrel having an inwardly directed shoulder at the second end for providing a valve seat for said flexible diaphragm means, said flexible diaphragm means being so constructed that it allows air to flow around its periphery through said second barrel in either direction when the air velocity is at a rate present while breathing normally through said tracheotomy tube and events into sealing engagement with said valve seat when air is exhaled through said tracheotomy tube at a rate above that present when breathing normally thereby blocking air flow through said second barrel, the distance between said diaphragm means and said valve seat being adjustable by rotation of said second barrel within said first barrel, and an outwardly directed flange on the second end of said second barrel extending outwardly past the sides of said first barrel for facilitating the manual rotation of said second barrel within said first barrel.

11. A valve for use with a tracheotomy tube comprising a first barrel having a passageway therethrough and a post in said passageway, said first barrel including means for connecting said passageway with a tracheotomy tube, means for centering said post in said passageway flexible circular diaphragm means located at one end of said first barrel whose center is attached to said post, and a second barrel having one end slidably inserted in said first barrel and having an air passageway therethrough and an annular shoulder at the other end which annular shoulder projects radially inward towards the center of said air passageway and defines a valve seat for said diaphragm means having an opening smaller than the surface area of said flexible diaphragm means, said flexible diaphragm means being so constructed that it allows air to flow around its periphery through said second barrel in either direction when the air velocity is at a rate present while breathing normally through said tracheotomy tube and everts into sealing engagement with said valve seat when air is exhaled through said tracheotomy tube at a rate above that present when breathing normally thereby blocking air flow through said second barrel, said second barrel having an inner diameter slightly larger than the diameter of said diaphragm thereby defining an annular space around the periphery of said flexible diaphragm means and means for adjusting the distance between said annular shoulder and said flexible diaphragm means for adjusting the rate of air flow around said flexible diaphragm means before said air passageway is blocked.

12. A valve according to claim 11 wherein said adjusting means comprises helical threads between said first and said second barrels for allowing said second barrel to be screwed a variable distance into said first barrel for varying the distance between said annular shoulder and said flexible diaphragm means.

13. A valve according to claim 12 wherein said centering means is a plurality of arms forming a spider at the end of said first barrel opposite said flexible diaphragm means, and said center post is connected at one end to the center of said spider and extends to said flexible diaphragm means on the central longitudinal axis of said first barrel.

14. A valve according to claim 13 wherein said second barrel has an outwardly directed flange on its free end, said outwardly directed flange having protuberances regularly spaced around its periphery and extending outwardly past the sides of said first barrel for facilitating manual rotation of said second barrel within said first barrel.

15. A valve according to claim 14 further comprising a tube sized to sealingly fit over said protuberances and said first barrel, said tube having a bend for shielding the air passageway through said valve body thereby blocking the entry of water when said valve is worn in a shower.

16. A valve according to claim 15 further comprising a filter connected to said tube for filtering air entering the air passageway through said valve body.

* * * * *

Notice of Adverse Decision in Interference

In Interference No. 101,290, involving Patent No. 4,325,366, C. J. Tabor, VALVE AND METHOD FOR USE WITH A TRACHEOTOMY TUBE, final judgment adverse to the patentee was rendered Sept. 17, 1987, as to claims 3-6 and 9-14.

[*Official Gazette November 21, 1989* ]